United States Patent
Huang et al.

(10) Patent No.: US 8,081,808 B2
(45) Date of Patent: Dec. 20, 2011

(54) RETINAL THICKNESS MEASUREMENT BY COMBINED FUNDUS IMAGE AND THREE-DIMENSIONAL OPTICAL COHERENCE TOMOGRAPHY

(75) Inventors: Yijun Huang, Pleasantville, NY (US); Tetsuyoshi Royama, Montvale, NJ (US); Alexandre Kotchkin, Ridgewood, NJ (US)

(73) Assignee: Topcon Medical Systems, Inc., Oakland, NJ (US)

( * ) Notice: Subject to any disclaimer, the term of this patent is extended or adjusted under 35 U.S.C. 154(b) by 646 days.

(21) Appl. No.: 12/262,620

(22) Filed: Oct. 31, 2008

(65) Prior Publication Data

US 2009/0123044 A1 May 14, 2009

Related U.S. Application Data

(60) Provisional application No. 61/002,345, filed on Nov. 8, 2007.

(51) Int. Cl.
*G06K 9/00* (2006.01)
*A61B 3/10* (2006.01)
*A61B 3/14* (2006.01)

(52) U.S. Cl. ............................ 382/128; 351/205; 351/206

(58) Field of Classification Search .................... None
See application file for complete search history.

(56) References Cited

U.S. PATENT DOCUMENTS

| | | | |
|---|---|---|---|
| 4,494,838 A * | 1/1985 | Wallquist et al. | 351/206 |
| 7,497,574 B2 * | 3/2009 | Watanabe et al. | 351/206 |
| 2005/0094099 A1 | 5/2005 | Newman et al. | |
| 2007/0195269 A1 | 8/2007 | Wei et al. | |
| 2007/0216909 A1 | 9/2007 | Everett et al. | |
| 2009/0033868 A1 * | 2/2009 | Huang et al. | 351/205 |
| 2009/0123036 A1 * | 5/2009 | Huang et al. | 382/117 |
| 2010/0290004 A1 * | 11/2010 | Huang et al. | 351/205 |
| 2010/0290005 A1 * | 11/2010 | Huang et al. | 351/206 |
| 2011/0043756 A1 * | 2/2011 | Kahn et al. | 351/206 |

FOREIGN PATENT DOCUMENTS

WO   WO2006/022045   3/2006

OTHER PUBLICATIONS

PCT International Search Report corresponding to PCT Application PCT/US2008/012506 filed Nov. 6, 2008 (4 pages).
PCT Written Opinion of the International Searching Authority corresponding to PCT Application PCT/US2008/012506 filed Nov. 6, 2008 (6 pages).
U.S. Appl. No. 11/800,186, filed May 4, 2007.

(Continued)

*Primary Examiner* — Jermele M Hollington
(74) *Attorney, Agent, or Firm* — Wolff & Samson PC

(57) ABSTRACT

Disclosed are method and apparatus for mapping retinal thickness values to a movable measurement grid. A three-dimensional volume dataset acquired from three-dimensional optical coherence tomography is registered to a fundus image by rendering a two-dimensional composite image from the three-dimensional volume dataset and superimposing characteristic features in the two-dimensional composite image upon corresponding characteristic features in the fundus image. A measurement grid is displayed on the two-dimensional composite image. The measurement grid is moved to a region of interest, and retinal thickness values in the region of interest are mapped to sectors within the measurement grid.

27 Claims, 14 Drawing Sheets

OTHER PUBLICATIONS

Bartlett, H. et al., "Use of Fundus Imaging in Quantification of Age-Related Macular Change", Survey of Ophthalmology, Survey of Ophthalmology Inc. vol. 52, No. 6, Nov. 18, 2007, pp. 655-671.

Paunescu L.A. et al., "Reproductibility of Nerve Fiber Thickness, Macular Thickness, and Optic Nerve Head Measurements Using StratusOCT", Invest. Ophthalmol. Vis. Sci., vol. 45, No. 6, Jun. 2004, pp. 1716-1724.

B. Cense, et. al. "Thickness and Birefringence of Healthy Retinal Nerve Fiber Layer Tissue Measured with Polarization-Sensitive Optical Coherence Tomography." Investigative Ophthalmology & Visual Science, Aug. 2004, vol. 45, No. 8, pp. 2606-2612.

M. Gabriele, et al. "Peripapillary Nerve Fiber Layer Thickness Profile Determined with High Speed, Ultrahigh Resolution Optical Coherence Tomography High-Density Scanning." Investigative Ophthalmology & Visual Science, Jul. 2007, vol. 48, No. 7, pp. 3154-3160.

H. Ishikawa, et. al. "Retinal Nerve Fiber Layer Assessment Using Optical Coherence Tomography with Active Optic Nerve Head Tracking." Investigative Ophthalmology & Visual Science, Mar. 2006, vol. 47, No. 3, pp. 964-967.

M. Sandberg, et al., "The Association Between Visual Acuity and Central Retinal Thickness in Retinitis Pigmentosa", Investigative Ophthalmology & Visual Science, Sep. 2005, vol. 46, No. 9, pp. 3349-3354.

A. Neubrauer, et al., "Tele-Screening for Diabetic Retinopathy with the Retinal Thickness Analyzer", Diabetes Care, vol. 26, No. 10, Oct. 2003, pp. 2890-2897.

* cited by examiner

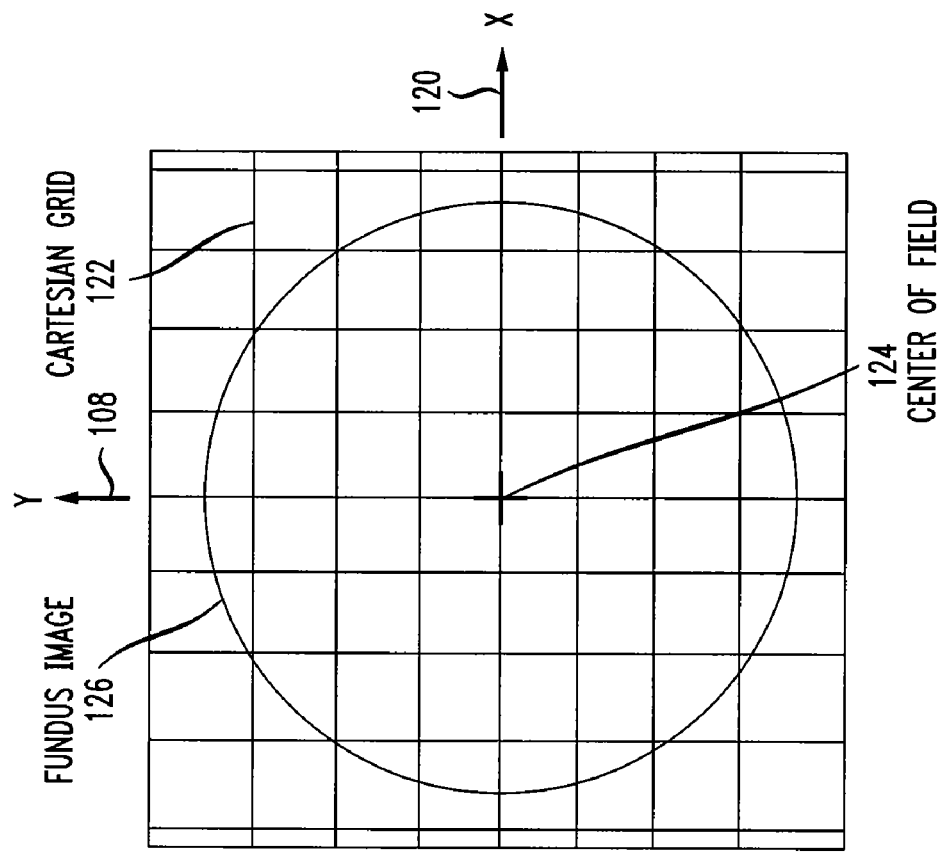
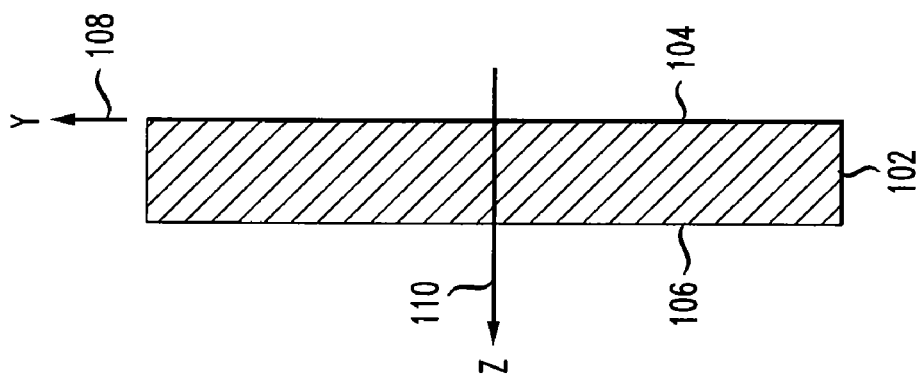

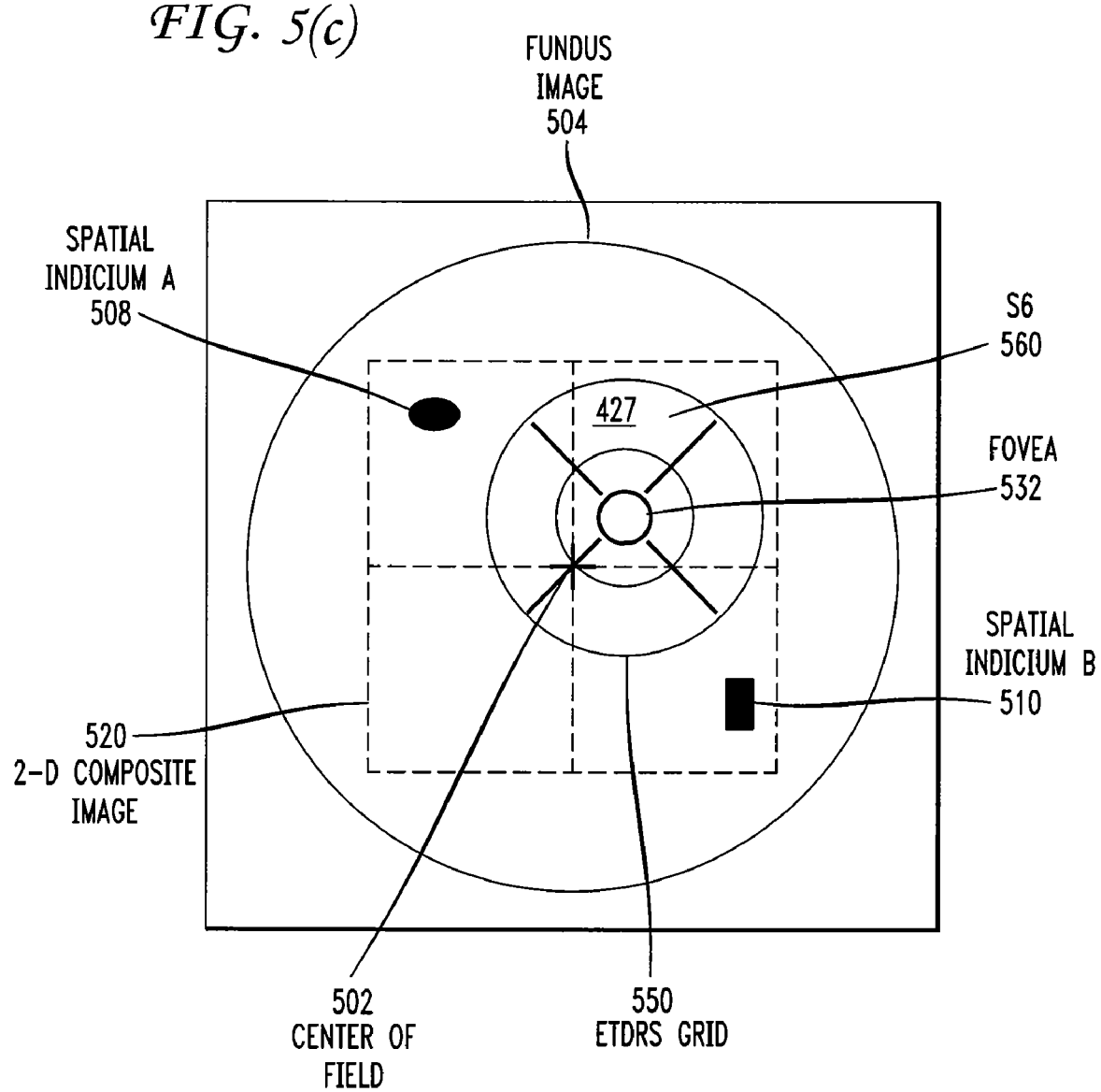

RETINAL THICKNESS MEASUREMENT BY COMBINED FUNDUS IMAGE AND THREE-DIMENSIONAL OPTICAL COHERENCE TOMOGRAPHY

This application claims the benefit of U.S. Provisional Application No. 61/002,345 filed Nov. 8, 2007, which is incorporated herein by reference.

BACKGROUND OF THE INVENTION

The present invention relates generally to ophthalmic characterization, and more particularly to mapping retinal thickness measurements to a movable measurement grid.

Diagnostics for eye disorders typically include a detailed ophthalmic examination of the retina. For initial examination, an eye doctor will view the retina through an ophthalmoscope. For a permanent record, the retina is typically photographed with a fundus camera. A fundus photograph directly records various anatomical features of the retina, such as the optic disc, fovea, blood vessels, and lesions. The imaging capabilities of fundus photography may be enhanced by supplementary techniques. A high-contrast image of retinal blood vessels, for example, may be photographed after the injection of a fluorescent dye into the bloodstream. The resulting image is referred to as a fluorescein angiogram (FA).

More sophisticated techniques have recently been developed for diagnostics of the eye. One such technique is three-dimensional optical coherence tomography (3-D OCT). In this technique, a light beam is directed onto the retina. Part of the beam is back-reflected. Interferometric analysis of the back-reflected light yields information on the structure of the retina. By varying optical parameters of the light probe, features at different depths below the surface of the retina may be probed. With this process, an image of a cross-section of the retina may be generated by scanning the optical probe along a line on the retina. By rastering the optical probe across the surface of the retina, a series of cross-sectional images may be produced. The series of cross-sectional images may be used to characterize the 3-D structure of the retina, and parameters such as local retinal thickness may be measured by 3-D OCT.

Analysis of the thickness of the retina may be used to diagnose diseases of the eye, for example, glaucoma and diabetic retinopathy. One indication of the health of the eye may be provided by comparing the retinal thickness of the patient's eye with reference data acquired from a population of healthy eyes. Progression of eye disease may also be monitored by measuring changes in retinal thickness over a period of time.

The retinal thickness is dependent on the loci (points on the retina) at which the measurements are made. The measurement loci are specified with respect to a reference point on the retina. Two common reference points are the center of the optic disc and the center of the fovea. One set of historical reference data from a large population of healthy retinas has been acquired with a Zeiss Stratus OCT 3, a commonly used instrument in the field of ophthalmology. This instrument measures the retinal thickness at loci on a circle centered at the center of the optic disc. The radius of the circle is fixed at 1.73 mm. Retinal thickness was also tracked in a large population of patients in the Early Treatment Diabetic Retinopathy Study (ETDRS). The center of the fovea was used as the reference point in that study.

For valid diagnostics, comparisons of the patient's data with the reference data must be determined at the same corresponding measurement loci. Errors will arise if the measurement loci in the patient's eye do not map properly to the measurement loci used for the reference data. A common assumption is that measurements by various instruments are properly referenced to the center of an anatomical feature such as the fovea. In some instances, this assumption may not hold, however. For example, the eye may move during examination. In some eyes, the fovea is off-centered in relation to the eye fixation point. Tracking progression of eye disease also requires that a patient's data is compared at the same set of measurement loci as a function of time. In addition, measuring retinal thickness in a neighborhood around a specific anatomical feature, such as a lesion, may be beneficial in diagnosing diseases of the eye.

What are needed are method and apparatus for mapping measurement loci to an anatomical feature and mapping retinal thickness values in a neighborhood around the anatomical feature.

BRIEF SUMMARY OF THE INVENTION

Summary values of a retinal parameter are mapped to a movable measurement grid. A fundus image of a retina is displayed. A two-dimensional composite image rendered from a three-dimensional volume dataset is registered to the fundus image by identifying characteristic features in the fundus image, identifying corresponding characteristic features in the two-dimensional composite image, and superimposing the characteristic features in the two-dimensional composite image onto the corresponding characteristic features in the fundus image. A measurement grid is displayed on the two-dimensional composite image and moved to a region of interest. Summary values within each neighborhood in the measurement grid are calculated from the three-dimensional volume dataset.

These and other advantages of the invention will be apparent to those of ordinary skill in the art by reference to the following detailed description and the accompanying drawings.

BRIEF DESCRIPTION OF THE DRAWINGS

FIG. 1(a) and FIG. 1(b) show a Cartesian coordinate system for the retina;

FIG. 5(c) shows a scenario in which the ETDRS grid has been repositioned over the off-centered fovea;

DETAILED DESCRIPTION

Figure 2:
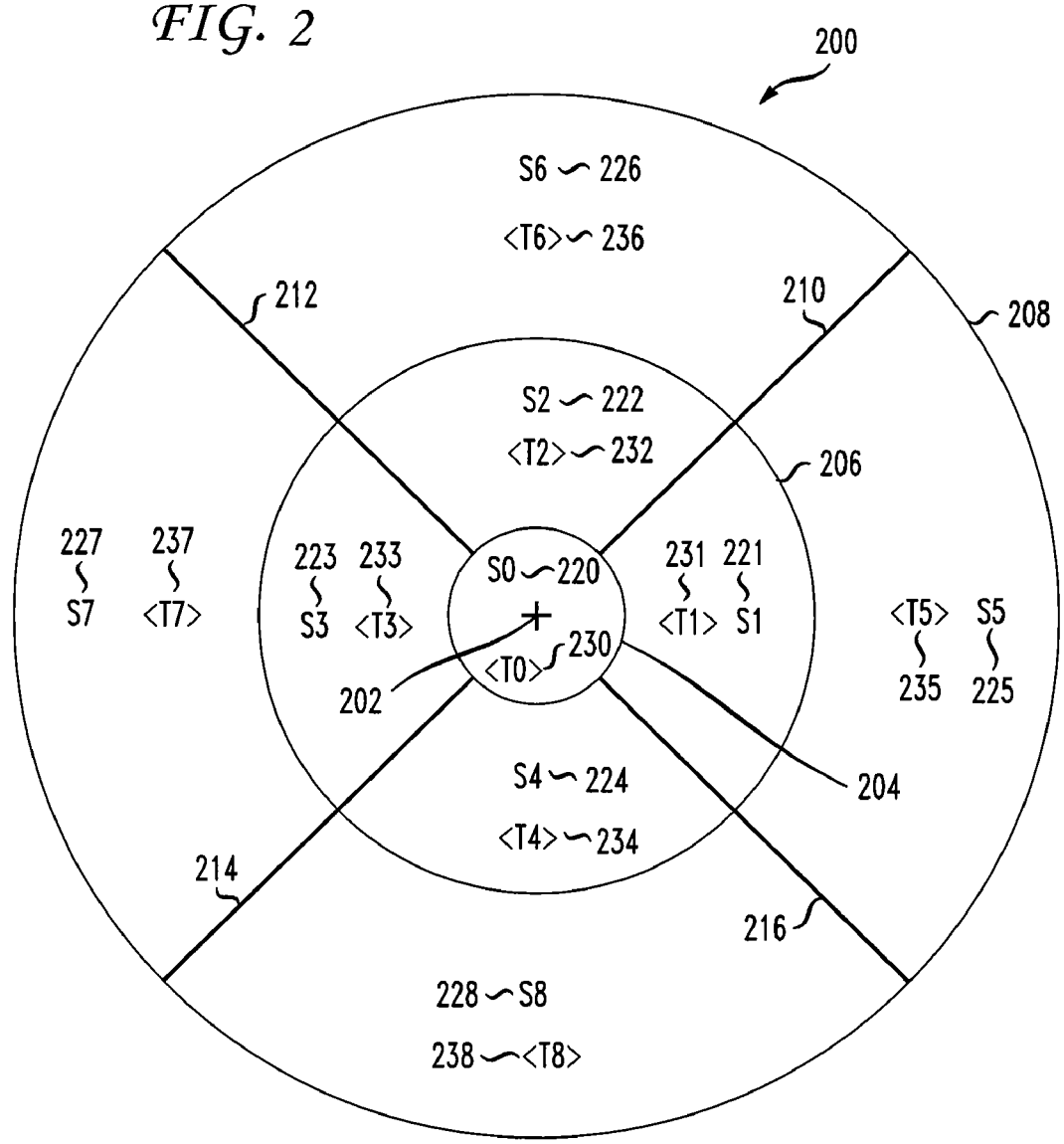
FIG. 2 shows an Early Treatment Diabetic Retinopathy Study (ETDRS) grid.

A powerful technique for characterizing and imaging ocular structures, including the retina, is three-dimensional optical coherence tomography (3-D OCT). In this technique, an optical probe, typically a laser beam, is directed onto the retina. Part of the beam is back-reflected. Interferometric analysis of the back-reflected light yields information on the structure of the retina. By varying optical parameters of the optical probe, features at different depths below the surface of the retina may be probed. With this process, an image of a cross-section of the retina may be generated by scanning the optical probe along a line on the retina. By rastering the optical probe across the surface of the retina, a series of cross-sectional images may be produced. The series of cross-sectional images characterize the 3-D structure of the retina, and parameters such as local retinal thickness may be measured by 3-D OCT.

A 3-D OCT scan measures back-reflected optical signals from a 3-D matrix of discrete points in a retina. Herein, a 3-D OCT volume dataset refers to a set of back-reflected optical signal intensities acquired from a 3-D matrix of discrete points in a retina. A 3-D graphical representation of a 3-D OCT volume dataset comprises a 3-D matrix of voxels, wherein a voxel corresponds to a graphical element at a discrete point in the retina. A 3-D volume dataset acquired from 3-D OCT scans may be rendered to display images on a two-dimensional (2-D) display, such as a computer monitor. The 3-D volume dataset, for example, may be mapped to luminance values of pixels for monochrome displays and luminance and false color values of pixels for color displays. Various images may be rendered from the 3-D volume dataset, for example, 2-D cross-sectional images, 2-D composite images, and 3-D perspective images. Herein, a 2-D composite image refers to a 2-D image rendered from a 3-D volume dataset and displayed on a user-defined plane. One skilled in the art may develop embodiments which apply to 3-D volume datasets acquired from other modalities.

Quantitative information, such as local retinal thickness, may be calculated from the 3-D OCT volume dataset. The retinal thickness varies with the position (locus) on the retina. The difference between the retinal layer thickness at a measurement locus on a patient's retina and a set of reference values may be used to characterize possible defects in the patient's retina. In general, a set of reference values is determined from a previous set of measurements at corresponding measurement loci. Of particular interest is a set of reference values derived from measurements acquired from a population of healthy retinas. Other sets of reference values, such as those indicative of certain diseases, may also be used.

Herein, a measurement locus on one retina corresponds to a measurement locus on a second retina if the position of the measurement locus on the first retina, relative to an anatomical feature on the first retina, is the same as the position of the measurement locus on the second retina, relative to the same anatomical feature on the second retina. For example, if the origin of a Cartesian coordinate system (see below) on the first retina is located at the center of the fovea on the first retina, and if the origin of a Cartesian coordinate system on the second retina is located at the center of the fovea on the second retina, then a measurement locus on the first retina corresponds to a measurement locus on the second retina if their Cartesian coordinates are the same (assuming the two Cartesian coordinate systems have the same scale and orientation). Herein, the first retina and the second retina may refer to two physically distinct retinas, or to the same physical retina at different times.

For proper comparison between the retinal layer thickness in a patient's retina with a set of reference values, the measurement locus on the patient's retina must be properly mapped to the corresponding measurement locus at which the set of reference values was measured. As discussed above, corresponding measurement loci may be referenced with respect to a common anatomical feature, such as the center of the optical disc or fovea. In the examples discussed below, the center of the fovea is used as the reference point. One skilled in the art, however, may develop embodiments in which the center of the optic disc, or other anatomical feature, is used as the reference point. Note that in some instances the shape of the fovea may be irregular, and the reference point, referred to as the nominal center, is chosen according to criteria defined by a user, such as an ophthalmologist. For simplicity, herein, the center of an anatomical feature refers to the geometric center of a feature with a true geometric center (such as a circle) and to the nominal center of a feature with irregular geometry.

Anatomical features are typically photographed by a fundus camera. The image may either be captured on film or stored in digital form and displayed on a monitor. In an embodiment, a 3-D OCT volume dataset is registered with specific anatomical features of the retina by registering a 2-D composite image (rendered from the 3-D OCT volume dataset) to a fundus image. Once the 3-D OCT volume dataset has been registered to the fundus image, retinal thickness measurements may be mapped to loci referenced to specific anatomical features. One skilled in the art may develop embodiments in which the 3-D OCT volume dataset is registered to a 2-D image produced by other modalities.

FIG. 1(a) and FIG. 1(b) show a reference coordinate system for a retina. FIG. 1(a) is a cross-sectional view, and FIG. 1(b) is a frontal view. Although a retina is a curved structure, it may be approximated by a planar structure, as represented in FIG. 1(a) by cross-section plane 102 with front surface plane 104 and rear surface plane 106. The front surface plane 104, for example, may be that which is viewed by an observer through an ophthalmoscope or photographed by a fundus camera. In a standard Cartesian coordinate system, the cross-section plane 102, as shown in FIG. 1(a), is the Y-Z plane, indicated by Y-axis 108 and Z-axis 110. The positive direction of Z runs from the front surface plane 104 to the rear surface plane 106, with Z=0 defined at the front surface plane 104. The Z-coordinate indicates the depth of a layer below the front surface plane 104.

The front surface plane 104 in FIG. 1(a), viewed along the +Z direction, is represented in FIG. 1(b) by the X-Y plane, indicated by X-axis 120 and Y-axis 108. Herein, the X-Y plane is also referred to as the retinal plane. The circle denoted Fundus Image 126 is a schematic representation of the field of a fundus image (no features are shown in this example). The origin of the Cartesian Grid 122 may be specified by a user, such as an ophthalmologist. In FIG. 1(b), the origin is placed at the center of Fundus Image 126, denoted Center of Field 124.

In an embodiment, retinal thickness is mapped to a measurement grid, such as a Cartesian grid or a radial grid. Herein, a measurement grid refers to a set of neighborhoods in which retinal thickness is measured. For example, in a Cartesian measurement grid such as Cartesian Grid 122 in FIG. 1(b), the neighborhoods are square regions. The retinal thickness is sampled at a set of measurement loci within each neighborhood. The number and configuration of the measurement loci within a neighborhood are defined by a user. The shape, size, and configuration of the neighborhoods within a measurement grid are defined by a user. Note that the shape, size, and configurations of the neighborhoods within a measurement grid do not need to be uniform (see discussion of an ETDRS grid below). The neighborhoods within a measurement grid do not need to be contiguous.

The Early Treatment Diabetic Retinopathy Study (ETDRS) grid, commonly used in ophthalmology, is shown in FIG. 2. The ETDRS Grid 200 comprises three concentric circles, Circle 204-Circle 208, centered at Center 202. Four radial lines, Radial Line 210-Radial Line 216, partition the measurement field into a measurement grid with nine sectors, labelled S0 220-S8 228. Sector S0 220 is the entire inner circular region contained within Circle 204. The other sectors, S1 221-S8 228, are portions (wedges) of annular rings. The sectors are examples of neighborhoods in a measurement grid. The center of the grid, Center 202, is referenced, for example, to the center of the fovea.

The retinal thickness within a sector is characterized by measuring the retinal thickness at a set of measurement loci within the sector. In an embodiment, retinal thicknesses are calculated from a 3-D volume dataset, such as a 3-D OCT volume dataset. Retinal thicknesses within a sector may be characterized by statistical values, herein referred to as summary values, such as average, median, minimum, maximum, standard deviation, quartile, interquartile mean, interquartile range, quantile, or percentile values. A summary value characterizing the retinal thickness within a sector is denoted herein as <T>. Herein, a summary value characterizing the retinal thickness within a sector is mapped to the sector. Herein, a set of summary values characterizing the retinal thickness over the region of the measurement grid are mapped to the measurement grid. In FIG. 2, for example, values <T0> 230-<T8> 238 are mapped to sectors S1 221-S8 228, respectively.

In general, a summary value of any retinal parameter may be mapped to a neighborhood in a measurement grid. Herein, a retinal parameter refers to any parameter which characterizes a property of the retina. Examples of retinal parameters include thickness, volume, density, diameters of anatomical features, and the number of anatomical features per unit area. In an embodiment, a summary value of a retinal parameter is calculated from a 3-D volume dataset, such as a 3-D OCT volume dataset. One skilled in the art may develop embodiments for retinal parameters other than retinal thickness.

Figure 3B:
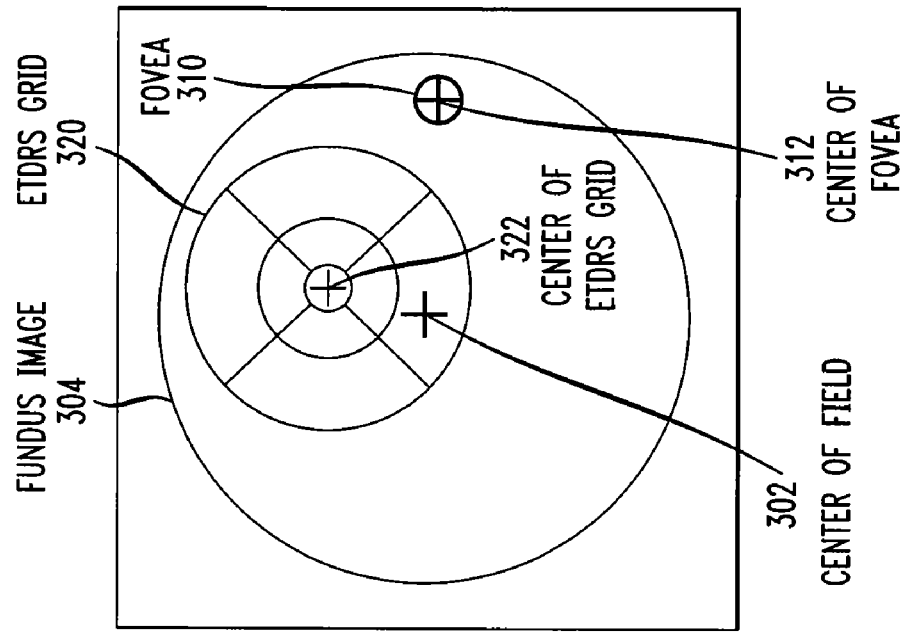
FIG. 3(b) shows a scenario in which the center of the fundus image, the center of the ETDRS grid, and the center of the fovea are displaced from each other.
Figure 3A:
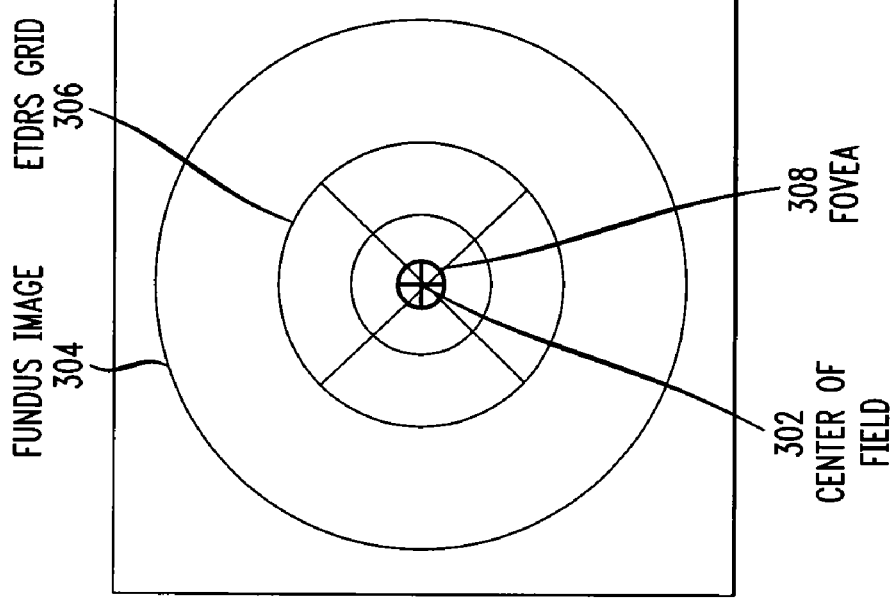
FIG. 3(a) shows a scenario in which a fundus image, an ETDRS grid, and a fovea have a common center point.

FIG. 3(a) shows a simplified example of a registration pattern for retinal measurements. Fundus Image 304, ETDRS Grid 306, and Fovea 308 all have a common center at the Center of Field 302. In general, however, ideal registration is not achieved under certain actual measurement conditions. For example, eye movement, asymmetric eye geometry, and instrument misalignment may result in improper registration. In the example shown in FIG. 3(b), Fundus Image 304, ETDRS Grid 320, and Fovea 310 are not properly registered. That is, Center of Field 302, Center of Fovea 312, and Center of ETDRS Grid 322 are displaced from one another.

Figure 4B:
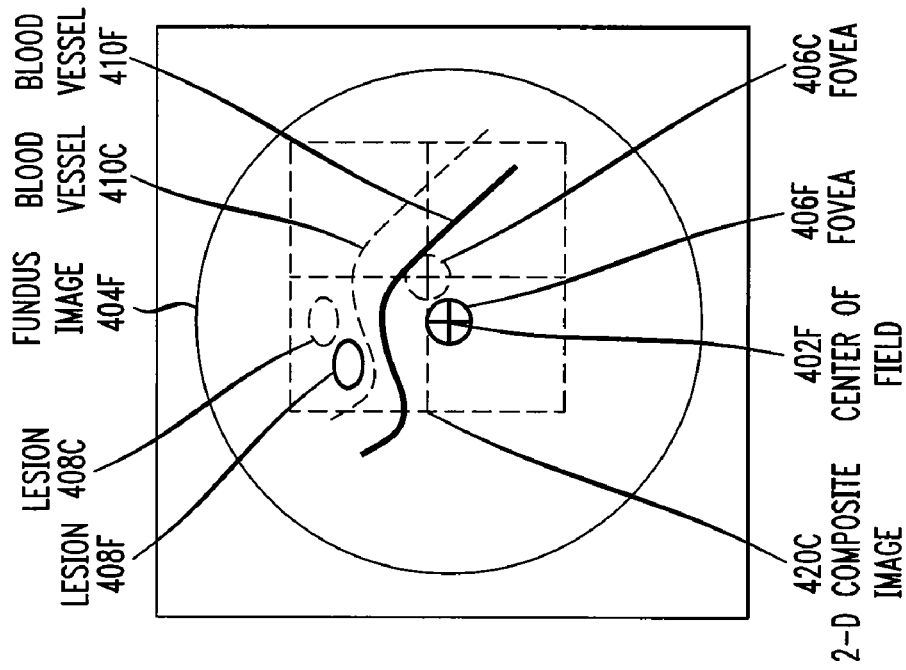
FIG. 4(b) shows schematic representations of corresponding characteristic features in a fundus image and in a two-dimensional composite image.
Figure 4A:
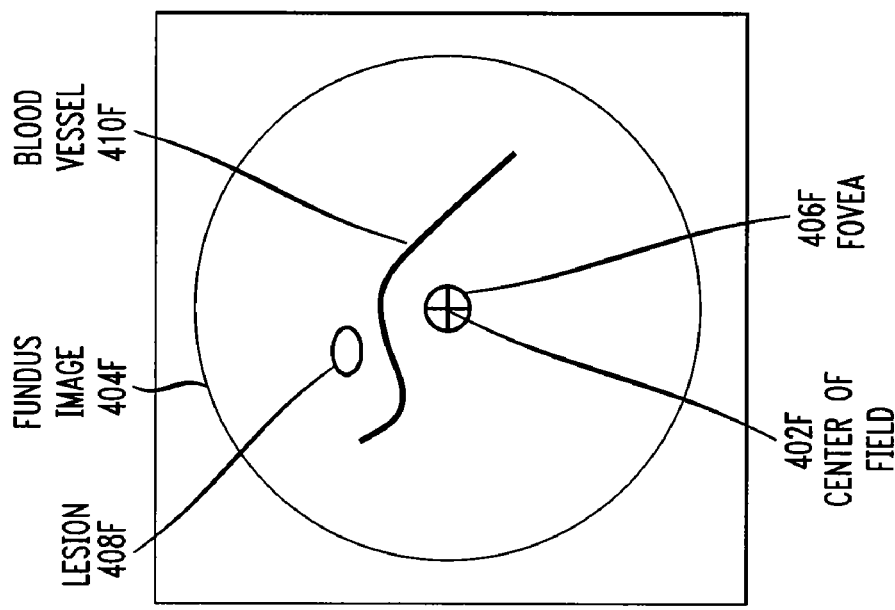
FIG. 4(a) shows schematic representations of characteristic features on a fundus image.

FIG. 4(a) and FIG. 4(b) illustrate an embodiment, as described in U.S. patent application Ser. No. 11/800,186, for registering a 3-D OCT volume dataset with a fundus image. In FIG. 4(a), the fundus image is schematically represented by Fundus Image 404F, centered at Center of Field 402F. Graphical representations of characteristic features, such as Fovea 406F, Lesion 408F, and Blood Vessel 410F, are shown. To simplify the terminology, herein, a "graphical representation of a characteristic feature" is also referred to simply as the "characteristic feature". Characteristic features are also referred to herein as landmarks or spatial indicia.

In FIG. 4(b), the dashed square, denoted 2-D Composite Image 420C, represents the field of a 2-D composite image rendered from a 3-D OCT volume dataset. In an embodiment, a 2-D composite image provides a frontal view, that is, a view corresponding to the fundus image. The 3-D OCT volume dataset may be registered to the fundus image by scaling, orienting, and aligning characteristic features in the 2-D composite image with the corresponding characteristic features in the fundus image. In FIG. 4(b), for example, characteristic features Fovea 406C, Lesion 408C, and Blood Vessel 410C in the 2-D Composite Image 420C correspond to characteristic features Fovea 406F, Lesion 408F, and Blood Vessel 410F in Fundus Image 404F. In this example, 2-D Composite Image 420C has already been processed to have the same scale and orientation as Fundus Image 404F; however, there is a uniform translation between the two images.

Herein, a characteristic feature in a first image corresponds to a characteristic feature in a second image, if the characteristic feature in the first image and the characteristic feature in the second image are the same. Herein, if a characteristic feature in a first image corresponds to a characteristic feature in the second image, then the characteristic feature in the second image also corresponds to the characteristic feature in the first image. Herein, a first image and a second image may be produced by different modalities (such as a fundus image and a 2-D composite image rendered from a 3-D OCT volume dataset) or by the same modality at different times. One skilled in the art may develop embodiments using modalities other than a fundus image or a 2-D composite image.

Figure 4C:
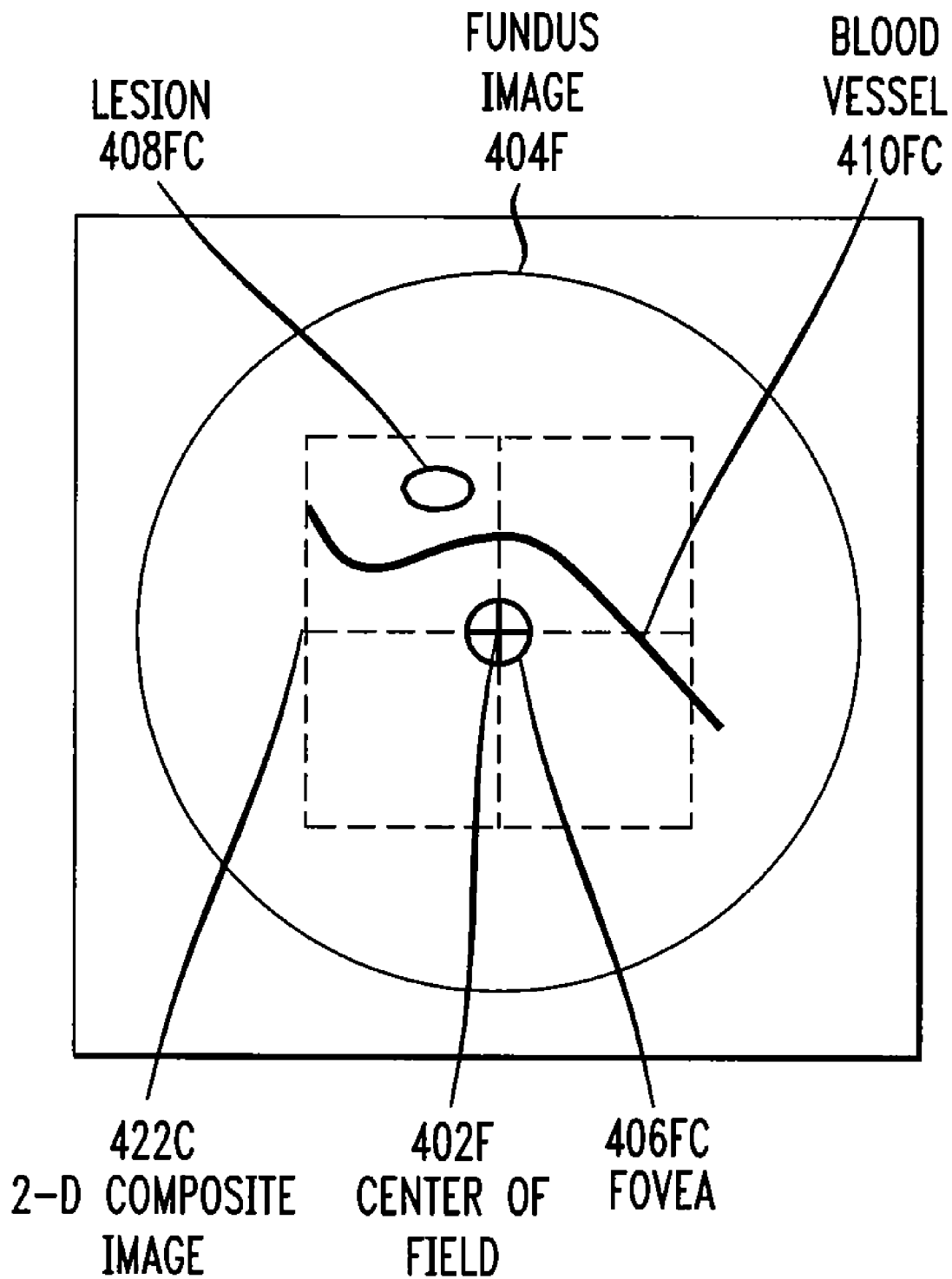
FIG. 4(c) shows a two-dimensional composite image superimposed onto a fundus image.
Figure 5A:
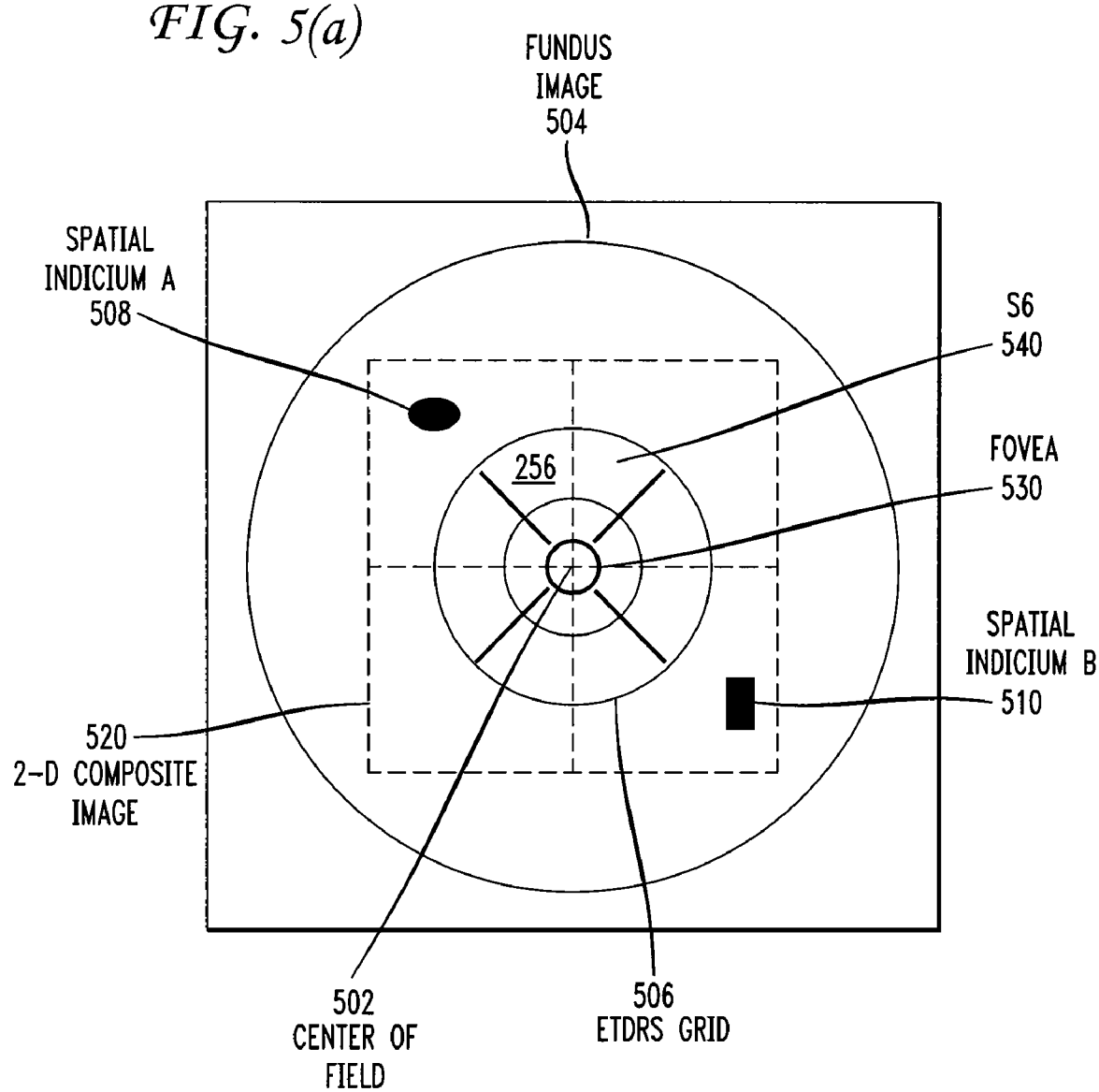
FIG. 5(a) shows a scenario in which a fundus image, an ETDRS grid, and a fovea have a common center point.
Figure 5B:
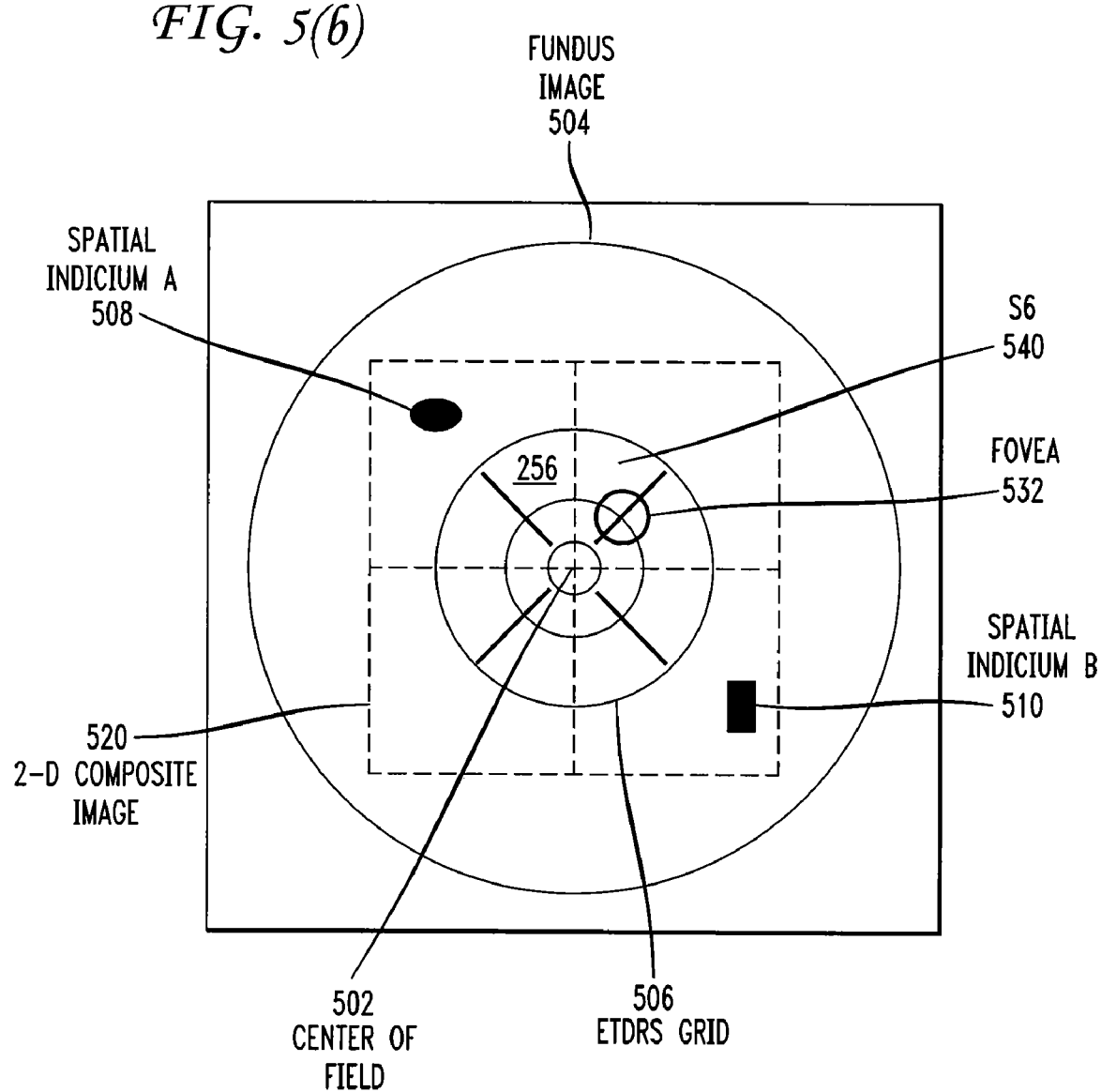
FIG. 5(b) shows a scenario in which the fovea is off-centered.
Figure 5D:
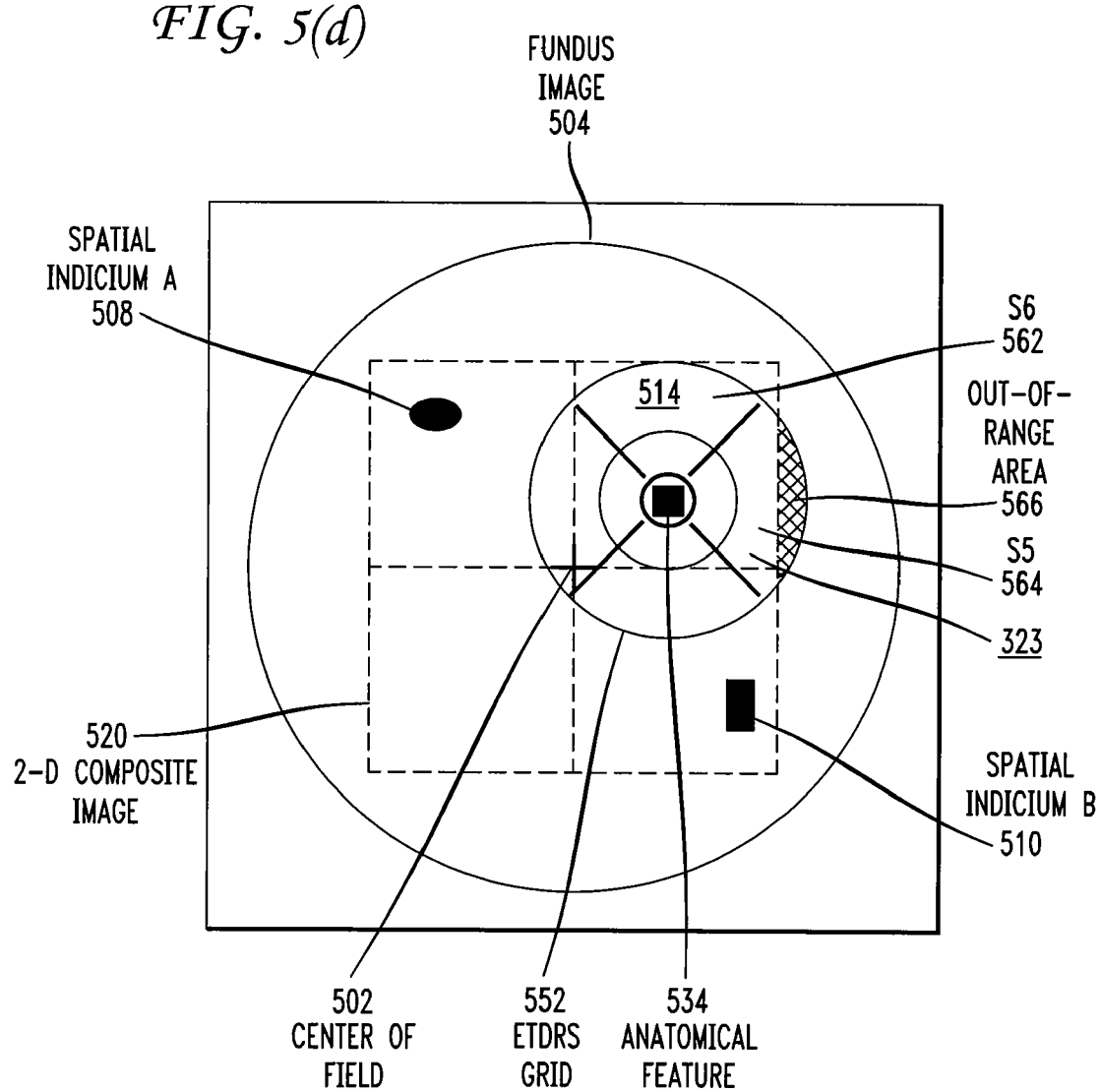
FIG. 5(d) shows a scenario in which a portion of a sector is out of range.
Figure 5E:
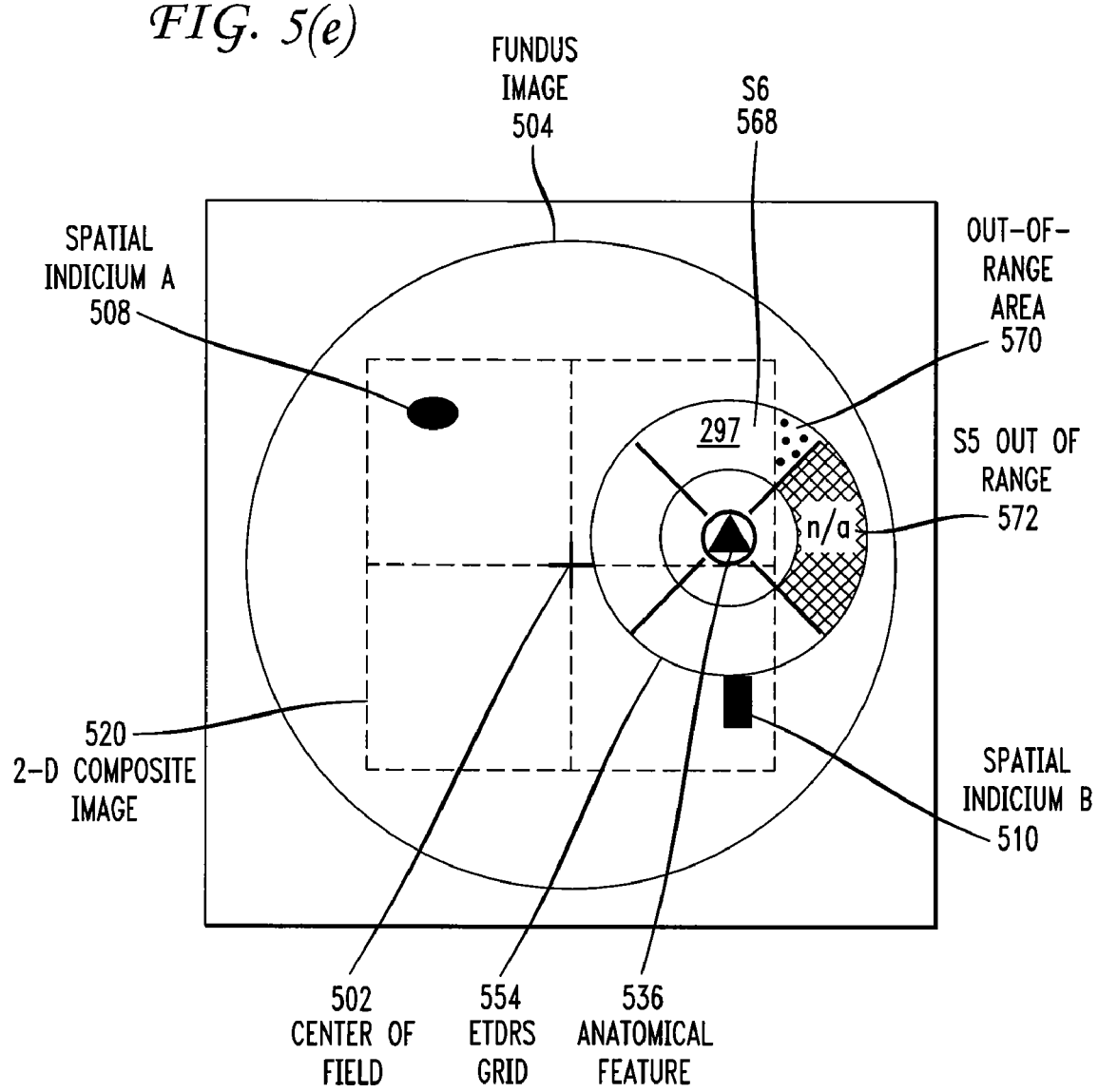
FIG. 5(e) shows a scenario in which a sector is completely out of range.
Figure 5F:
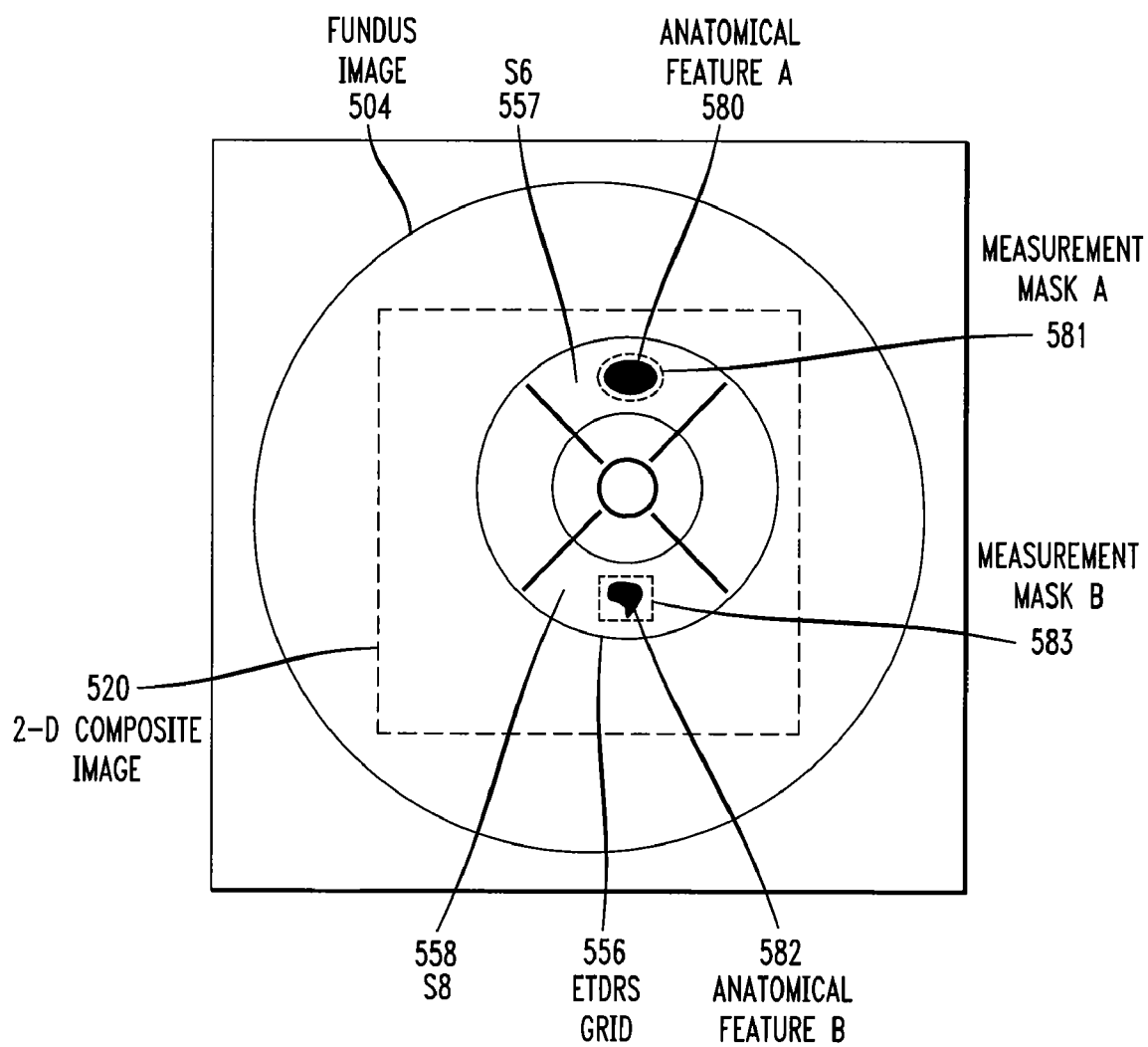
FIG. 5(f) shows an ETDRS grid with masked regions.
Figure 5G:
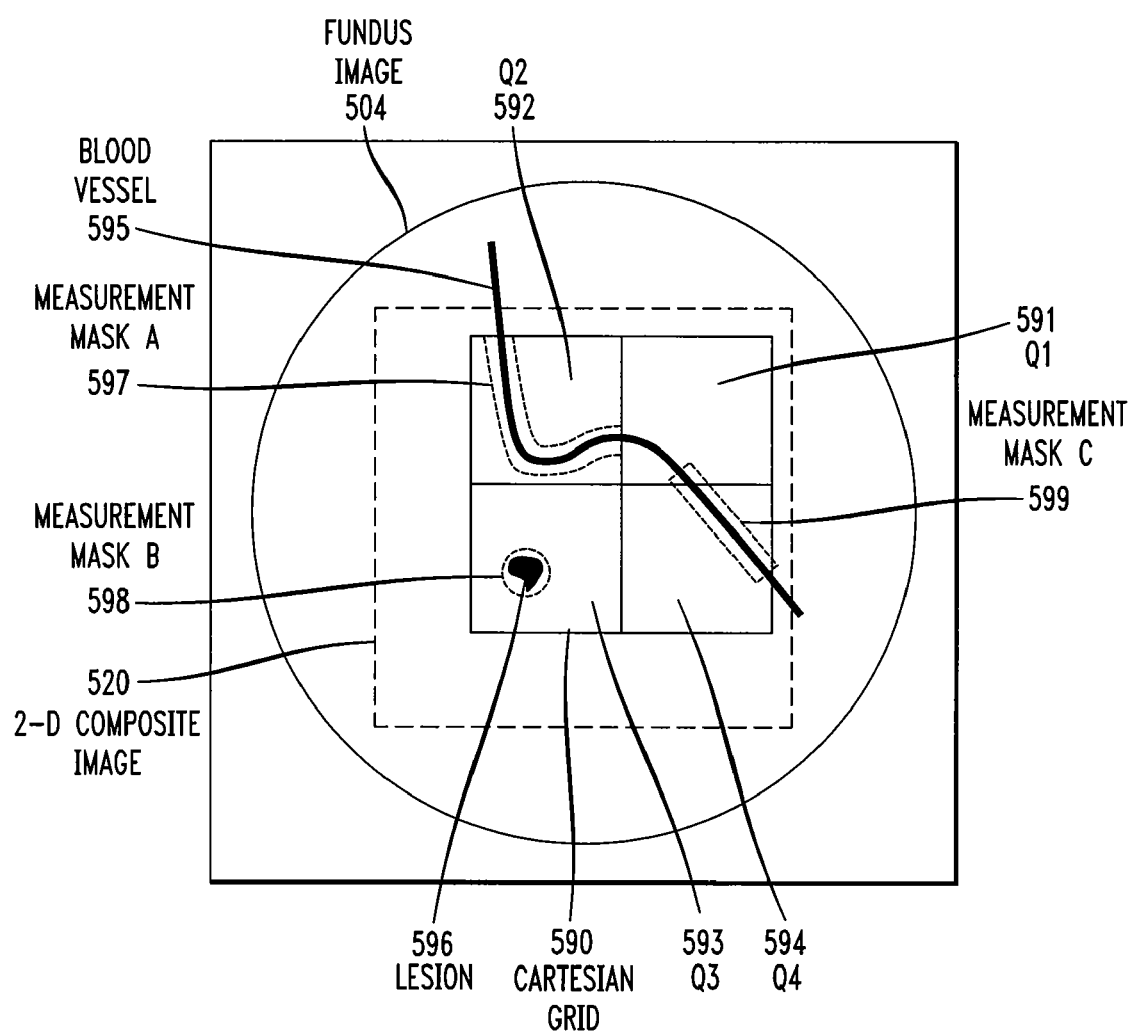
FIG. 5(g) shows a Cartesian grid with masked regions.

In an embodiment, Fundus Image 404F and 2-D Composite Image 420C are displayed on a monitor. The Fundus Image 404F remains fixed in the field of view, while the 2-D Composite Image 420C may be freely moved. For example, a user may use a mouse to position a cursor on 2-D Composite Image 420C, click on it, and drag it over Fundus Image 404F until characteristic features Fovea 406C, Lesion 408C, and Blood Vessel 410C in the 2-D Composite Image 420C are superimposed onto the corresponding characteristic features Fovea 406F, Lesion 408F, and Blood Vessel 410F in Fundus Image 404F. The results are shown in FIG. 4(c), in which the characteristic features in the superimposed images are denoted Fovea 406FC, Lesion 408FC, and Blood Vessel 410FC. In an embodiment, the user may also change the scale and orientation of 2-D Composite Image 420C. In an embodiment, superposition of characteristic features in 2-D Composite Image 420C onto corresponding characteristic features in Fundus Image 404F may be performed with automatic image recognition and processing. Note that superposition of multiple corresponding characteristic features provides more precise registration than superposition of a single characteristic feature, such as the fovea. Since, in general, characteristic features may have irregular shapes, and their boundaries may not be distinct, the precision of registration improves as the number of corresponding characteristic features increases.

In an embodiment, once the 3-D OCT volume dataset has been properly registered to the fundus image, a ETDRS grid, or other measurement grid (such as a Cartesian grid), may be digitally generated and superimposed onto the 2-D composite image and fundus image. In the example shown in FIG. 5(a), Fundus Image 504 is centered at Center of Field 502. The 2-D Composite Image 520 has been superimposed onto Fundus Image 504 by using the characteristic features denoted Spatial Indicium A 508 and Spatial Indicium B 510, which, for example, may be lesions or other anatomical features. In the example shown in FIG. 5(*a*), the Fovea 530 is also used as a characteristic feature for registration. The center of Fovea 530 is the Center of Field 502. The ETDRS Grid 506 is superimposed onto the 2-D Composite Image 520 and onto the Fundus Image 504. In an embodiment, the summary value <T> characterizing the retinal thickness within a sector (such as average or median value) is displayed in each sector, as shown previously in FIG. 2. In FIG. 5(*a*), for example, the value 256 in sector S6 540, indicates an average value of 256 microns.

In the example shown in FIG. 5(*b*), the Fovea 532 is not centered on the Center of Field 502. Therefore, retinal thicknesses with respect to the ETDRS Grid 506 centered on the Center of Field 502 are not properly specified relative to the center of the Fovea 532. For example, the average retinal thickness in sector S6 540 is now indicated as 138 microns. In an embodiment, shown in FIG. 5(*c*), the 2-D Composite Image 520 is held fixed, while the ETDRS grid may be freely moved (positioned). For example, a user may use a mouse to position a cursor on ETDRS Grid 550, click on it, and drag it until the center of ETDRS Grid 550 is aligned with the center of Fovea 532. Summary values characterizing retinal thickness within each sector of ETDRS Grid 550 are then measured with respect to the center of the Fovea 532. For example, the average value of retinal thickness in sector S6 560 is 427 microns.

FIG. 5(*d*) shows an embodiment in which the ETDRS grid is moved until it is centered on an anatomical feature other than the fovea. This capability, for example, may be used to characterize retinal thickness in a neighborhood around a defect such as Anatomical Feature 534. Herein, the region of the retina which is to be analyzed is also referred to as the region of interest. To simplify the figure, the fovea is not shown. The average thickness in sector S6 562 is 514 microns. Note that part of sector S5 564 is now out of range. Calculation of the retinal thickness from the 3-D OCT volume dataset is valid only within the region of 2-D Composite Image 520. Herein, an area or region is out of range if it lies outside of the 2-D composite image. The out-of-range area is shown schematically as the cross-hatched Out-of-Range Area 566. In an embodiment, if there are sufficient valid data points in the in-range region of sector S5 564, summary values of the retinal thickness over the in-range region are calculated. For example, the average retinal thickness for the in-range region of sector S5 564 is 323 microns. The criteria for determining whether there are a sufficient number of valid data points over a particular in-range region is specified by a user, such as an ophthalmologist.

In FIG. 5(*e*), ETDRS Grid 554 is centered on Anatomical Feature 536. A portion of sector S6 568 is out of range. This portion is schematically indicated by the dotted region, Out-of-Range Area 570. The average thickness over the in-range region of sector S6 568 is 297 microns. Note that sector S5 572 is entirely out of range. In this instance, an error message such as "not/applicable (n/a)" or "invalid" is displayed.

In an embodiment, a user-specified region may be excluded from a measurement grid. No measurements at loci within the user-specified region are taken. More than one user-specified region may be excluded from a measurement grid. An entire neighborhood may be excluded from a measurement grid. In an embodiment, the user-specified region from which measurements are excluded is graphically indicated by a measurement mask on the measurement grid. Herein, excluding measurements from a user-specified region is also referred to as masking a set of measurement loci within the measurement grid. The set of measurement loci do not need to be contiguous.

In the example shown in FIG. 5(*f*), the measurement grid is ETDRS Grid 556. Located in sector S6 557 is Anatomical Feature A 580. In a specific measurement procedure, retinal thickness measurements are taken at the full set of measurement loci within sector S6 557, and summary values for sector S6 557 are calculated from the full set of measurements. These measurements include anomalous values on or near Anatomical Feature A 580. In an embodiment, a user may place a measurement mask, denoted Measurement Mask A 581, over Anatomical Feature A 580. Measurements at measurement loci within the retinal region defined by Measurement Mask A 581 are excluded from the calculation of summary values. The effect of Anatomical Feature A 580 on a summary value, such as mean retinal thickness, in sector S6 557 may be determined by comparing the mean retinal thickness with and without Measurement Mask A 581 in place. Similarly, Anatomical Feature 582 is located in sector S8 558. The effect of Anatomical Feature 582 on a summary value, such as the $95^{th}$ percentile of the retinal thickness, in sector S8 558 may be determined by comparing the summary values with and without Measurement Mask B 583 in place.

The size, shape, position, and orientation of a measurement mask are controlled by a user. In FIG. 5(*f*), Anatomical Feature A 580 has a nearly elliptical shape. Therefore, a user may choose an elliptical shape for Measurement Mask A 581. In an embodiment, a palette of shapes is displayed on a graphical user interface (GUI). A user may use a mouse to click on a specific shape, such as an ellipse, drag it over Anatomical Feature A 580, and adjust the size, aspect ratio, and orientation of Measurement Mask A 581. Anatomical Feature B 582 in sector S8 558 has an irregular shape. In this instance, a user may choose a square shape for Measurement Mask B 583.

A more complicated example is shown in FIG. 5(*g*). Here the measurement grid is Cartesian Grid 590, which is divided into four quadrants, denoted Q1 591-Q4 594. Blood Vessel 595 runs through Q1 591, Q2 592, and Q4 594. Lesion 596 is present in Q3 593. In this example, Measurement Mask B 598 has a circular shape, and Measurement Mask C 599 has a rectangular shape. Measurement Mask A 597 is a conformal mask which follows the contour of the portion of Blood Vessel 595 within quadrant Q2 592. Measurement Mask A 597, for example, may be traced on a GUI with a mouse or digital stylus.

Figure 6:
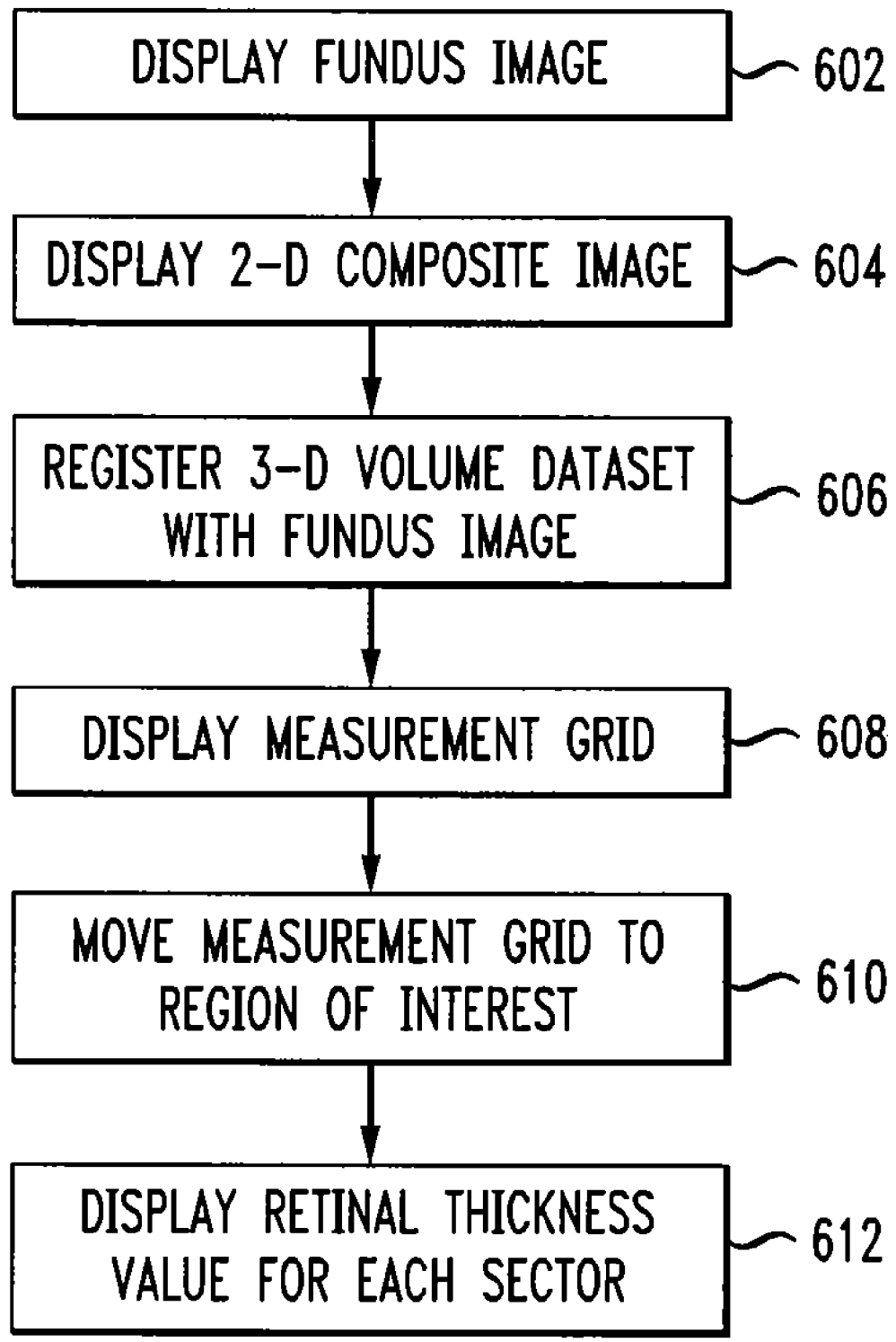
FIG. 6 shows a flowchart of steps for displaying values of retinal thickness mapped to a movable grid.

FIG. 6 shows a flowchart of steps for displaying retinal thickness values over a user-defined region of the retina. In step 602, a fundus image (for example, Fundus Image 404F in FIG. 4(*a*)) is displayed on a monitor. The process then passes to step 604, in which a 2-D composite image (for example, 2-D Composite Image 420C in FIG. 4(*b*)) is rendered from a 3-D OCT volume dataset and displayed on the same monitor. The process then passes to step 606, in which the 3-D OCT volume dataset is registered with the fundus image. Characteristic features, such as Lesion 408F, Blood Vessel 410F, and Fovea 406F in FIG. 4(*a*), are first identified on Fundus Image 404F. Corresponding characteristic features, such as Lesion 408C, Blood Vessel 410C, and Fovea 406C are identified on 2-D Composite Image 420C. Registration is achieved by moving 2-D Composite Image 420C until the characteristic features in 2-D Composite Image 420C are superimposed onto the corresponding characteristic features in Fundus Image 404F.

The process then passes to step 608, in which a measurement grid (for example, ETDRS Grid 506 in FIG. 5(*a*)) is displayed on the monitor. The process then passes to step 610, in which the measurement grid is moved to the region of interest. For example, in FIG. 5(d), ETDRS Grid 552 is moved until its center is aligned with the center of Anatomical Feature 534. The process then passes to step 612, in which a retinal thickness value (such as average or median) characterizing each sector is calculated from the 3-D OCT volume dataset and displayed within each sector. For example, in FIG. 5(d), the average thickness value for sector S6 562 is 514 microns.

Figure 7:
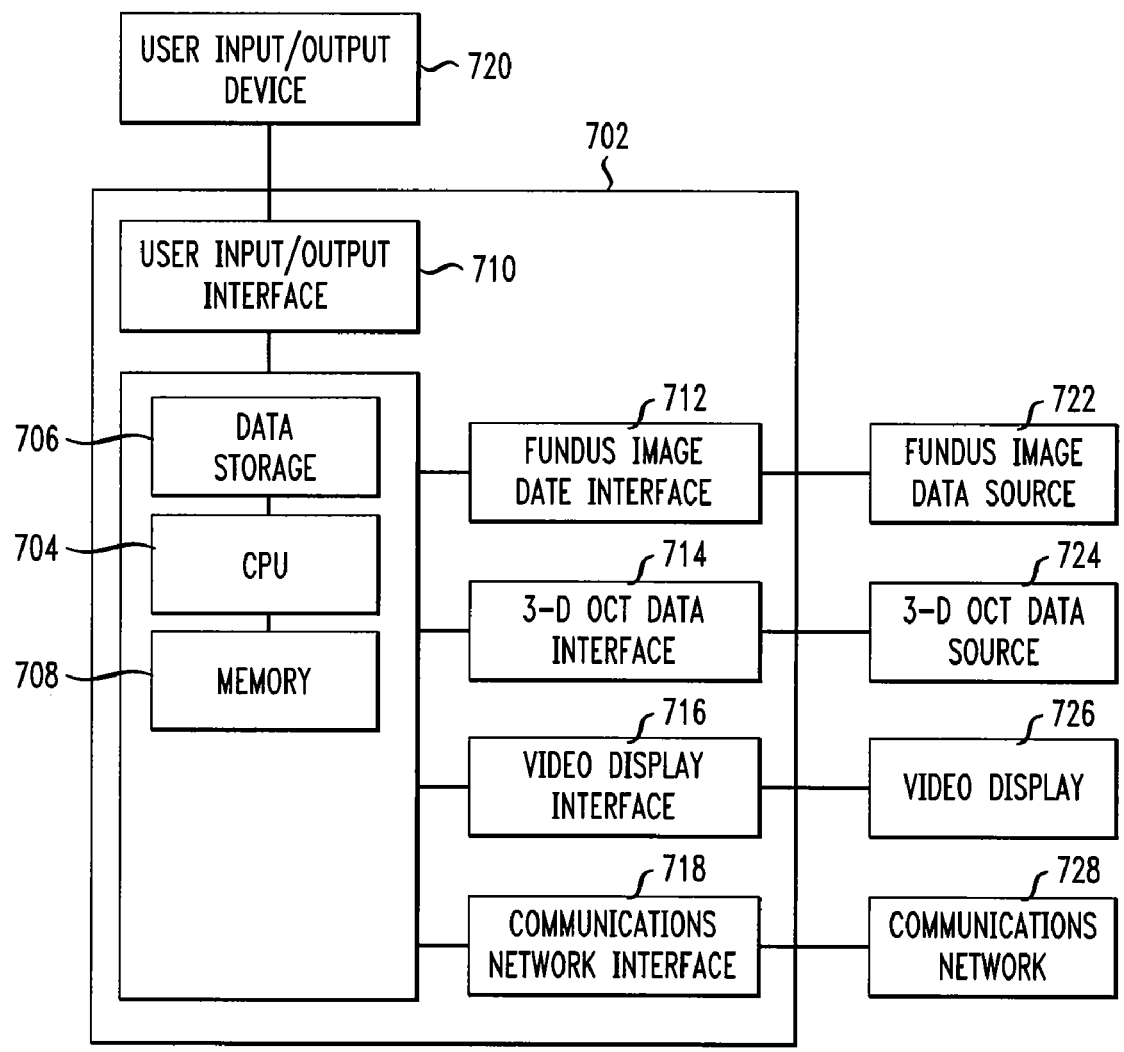
FIG. 7 is a schematic of a measurement and image processing system implemented with a computer.

One embodiment of a measurement and image processing system for mapping retinal thickness over different regions of the retina defined by a movable grid may be implemented using a computer. For example, the steps shown in the flowchart in FIG. 6 may be performed with a computer. As shown in FIG. 7, computer 702 may be any type of well-known computer comprising a central processing unit (CPU) 704, memory 708, data storage 706, and user input/output interface 710. Data storage 706 may comprise a hard drive or non-volatile memory. User input/output interface 710 may comprise a connection to a user input device 720, such as a keyboard or mouse. For example, computer 702 may receive user input from user input device 720 to move 2-D Composite Image 420C (in FIG. 4(b)) or ETDRS Grid 550 (in FIG. 5(c)). As is well known, a computer operates under control of computer software which defines the overall operation of the computer and applications. CPU 704 controls the overall operation of the computer and applications by executing computer program instructions which define the overall operation and applications. The computer program instructions may be stored in data storage 706 and loaded into memory 708 when execution of the program instructions is desired.

Computer 702 may further comprise a video display interface 716, which may transform signals from CPU 704 to signals which may drive video display 726. Computer 702 may further comprise one or more network interfaces. For example, communications network interface 718 may comprise a connection to an Internet Protocol (IP) communications network 728, which may transport test data or user test data and commands.

Computer 702 may further comprise fundus image data interface 712 which may provide communication between computer 702 and fundus image data source 722, which may, for example, be a digital fundus camera. Computer 702 may further comprise 3-D OCT data interface 714, which may, for example, provide communication between computer 702 and 3-D OCT data source 724, which may, for example, be a 3-D OCT ophthalmic diagnostic instrument. In an embodiment, fundus image data source 722 and 3-D OCT data source 724 may be databases which may be transferred to data storage 706 via fundus image data interface 712 and 3-D OCT data interface 714. Databases may also be transferred to data storage 706 via communications network 728 and communications network interface 718. Computers are well known in the art and will not be described in detail herein.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for mapping a plurality of summary values of a retinal parameter to a measurement grid comprising a plurality of neighborhoods, comprising the steps of:
    displaying a fundus image;
    rendering a two-dimensional composite image from a three-dimensional volume dataset;
    registering the two-dimensional composite image to the fundus image;
    displaying the measurement grid on the two-dimensional composite image;
    moving, in response to user input, the measurement grid to a region of interest; and
    calculating at least one of said plurality of summary values in each of said plurality of neighborhoods.

2. The method of claim 1, further comprising the step of:
    displaying a numerical value of at least one of said plurality of summary values in each of said plurality of neighborhoods.

3. The method of claim 1, further comprising the step of:
    masking a set of measurement loci within said measurement grid.

4. The method of claim 1, further comprising the step of:
    acquiring said three-dimensional volume dataset by three-dimensional optical coherence tomography.

5. The method of claim 1, wherein the step of registering the two-dimensional composite image to the fundus image further comprises the steps of:
    displaying at least one characteristic feature on said fundus image;
    displaying at least one corresponding characteristic feature on said two-dimensional composite image; and
    superimposing, in response to user input, said at least one corresponding characteristic feature onto said at least one characteristic feature.

6. The method of claim 1, wherein the step of displaying the measurement grid on the two-dimensional composite image further comprises the step of:
    displaying an Early Treatment Diabetic Retinopathy Study (ETDRS) grid.

7. The method of claim 1, wherein the step of displaying the measurement grid on the two-dimensional composite image further comprises the step of:
    displaying a Cartesian grid.

8. The method of claim 1, wherein the plurality of summary values comprises at least one of:
    an average value of a retinal thickness;
    a median value of a retinal thickness;
    a standard deviation value of a retinal thickness;
    a quartile value of a retinal thickness;
    an interquartile range of a retinal thickness;
    an interquartile mean of a retinal thickness;
    a quantile value of a retinal thickness;
    a percentile value of a retinal thickness;
    a maximum value of a retinal thickness; and
    a minimum value of a retinal thickness.

9. The method of claim 1, wherein the step of calculating further comprises the step of:
    calculating from said three-dimensional volume dataset.

10. An apparatus for mapping a plurality of summary values of a retinal parameter to a measurement grid comprising a plurality of neighborhoods, comprising:
    means for displaying a fundus image;
    means for rendering a two-dimensional composite image from a three-dimensional volume dataset;
    means for registering the two-dimensional composite image to the fundus image;

means for displaying the measurement grid on the two-dimensional composite image;
means for moving, in response to user input, the measurement grid to a region of interest; and
means for calculating at least one of said plurality of summary values in each of said plurality of neighborhoods.

11. The apparatus of claim 10, further comprising:
means for displaying a numerical value of at least one of said plurality of summary values in each of said plurality of neighborhoods.

12. The apparatus of claim 10, further comprising:
means for masking a set of measurement loci within said measurement grid.

13. The apparatus of claim 10, further comprising:
means for acquiring said three-dimensional volume dataset by three-dimensional optical coherence tomography.

14. The apparatus of claim 10, wherein the means for registering the two-dimensional composite image to the fundus image further comprise:
means for displaying at least one characteristic feature on said fundus image;
means for displaying at least one corresponding characteristic feature on said two-dimensional composite image; and
means for superimposing, in response to user input, said at least one corresponding characteristic feature onto said at least one characteristic feature.

15. The apparatus of claim 10, wherein the means for displaying the measurement grid on the two-dimensional composite image further comprises:
means for displaying an Early Treatment Diabetic Retinopathy Study (ETDRS) grid.

16. The apparatus of claim 10, wherein the means for displaying the measurement grid on the two-dimensional composite image further comprises:
means for displaying a Cartesian grid.

17. The apparatus of claim 10, wherein the plurality of summary values comprises at least one of:
an average value of a retinal thickness;
a median value of a retinal thickness;
a standard deviation value of a retinal thickness;
a quartile value of a retinal thickness;
an interquartile range of a retinal thickness;
an interquartile mean of a retinal thickness;
a quantile value of a retinal thickness;
a percentile value of a retinal thickness;
a maximum value of a retinal thickness; and
a minimum value of a retinal thickness.

18. The apparatus of claim 10, wherein the means for calculating further comprises:
means for calculating from said three-dimensional volume dataset.

19. A computer readable medium storing computer instructions for mapping a plurality of summary values of a retinal parameter to a measurement grid comprising a plurality of neighborhoods, the computer instructions defining the steps of:
displaying a fundus image;
rendering a two-dimensional composite image from a three-dimensional volume dataset;
registering the two-dimensional composite image to the fundus image;
displaying the measurement grid on the two-dimensional composite image;
moving, in response to user input, the measurement grid to a region of interest; and
calculating at least one of said plurality of summary values in each of said plurality of neighborhoods.

20. The computer readable medium of claim 19, wherein the computer instructions further comprise computer instructions defining the step of:
displaying a numerical value of at least one of said plurality of summary values in each of said plurality of neighborhoods.

21. The computer readable medium of claim 19, wherein the computer instructions further comprise computer instructions defining the step of:
masking a set of measurement loci within said measurement grid.

22. The computer readable medium of claim 19, wherein the computer instructions further comprise computer instructions defining the step of:
acquiring said three-dimensional volume dataset by three-dimensional optical coherence tomography.

23. The computer readable medium of claim 19, wherein the computer instructions defining the step of registering the two-dimensional composite image to the fundus image further comprise computer instructions defining the steps of:
displaying at least one characteristic feature on said fundus image;
displaying at least one corresponding characteristic feature on said two-dimensional composite image; and
superimposing, in response to user input, said at least one corresponding characteristic feature onto said at least one characteristic feature.

24. The computer readable medium of claim 19, wherein the computer instructions defining the step of displaying the measurement grid on the two-dimensional composite image further comprise computer instructions defining the step of:
displaying an Early Treatment Diabetic Retinopathy Study (ETDRS) grid.

25. The computer readable medium of claim 19, wherein the computer instructions defining the step of displaying the measurement grid on the two-dimensional composite image further comprise computer instructions defining the step of:
displaying a Cartesian grid.

26. The computer readable medium of claim 19, wherein the plurality of summary values comprises at least one of:
an average value of a retinal thickness;
a median value of a retinal thickness;
a standard deviation value of a retinal thickness;
a quartile value of a retinal thickness;
an interquartile range of a retinal thickness;
an interquartile mean of a retinal thickness;
a quantile value of a retinal thickness;
a percentile value of a retinal thickness;
a maximum value of a retinal thickness; and
a minimum value of a retinal thickness.

27. The computer readable medium of claim 19, wherein the computer instructions defining the step of calculating further comprise computer instructions defining the step of:
calculating from said three-dimensional volume dataset.

* * * * *